(12) United States Patent
Suddaby

(10) Patent No.: US 6,436,103 B1
(45) Date of Patent: Aug. 20, 2002

(54) DRILL GUIDE AND PLATE ATTACHMENT MECHANISM FOR ORTHOPEDIC PLATING

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 2 days.

(21) Appl. No.: 09/741,752

(22) Filed: Dec. 21, 2000

(51) Int. Cl.⁷ .............................................. A61B 17/80
(52) U.S. Cl. .......................................... 606/96; 606/69
(58) Field of Search .............................. 606/60, 69, 70, 606/96, 99, 72, 61

(56) References Cited

U.S. PATENT DOCUMENTS

| | | | | |
|---|---|---|---|---|
| 2,500,370 A | * | 3/1950 | McKibbin | 606/69 |
| 5,290,281 A | * | 3/1994 | Tschakaloff | 606/28 |
| 5,423,826 A | * | 6/1995 | Coates et al. | 606/96 |
| 5,549,612 A | * | 8/1996 | Yapp et al. | 606/69 |
| 6,168,596 B1 | * | 1/2001 | Wellisz et al. | 606/69 |
| D440,311 S | * | 4/2001 | Michelson | D24/155 |

* cited by examiner

Primary Examiner—Jeffrey A. Smith
Assistant Examiner—Michael B. Priddy
(74) Attorney, Agent, or Firm—Shoemaker and Mattare

(57) ABSTRACT

An orthopedic plate is provided with recesses specially adapted to be engaged by the jaws of a drill guide tool, whereby the plate can be held while holes are being drilled through the plate into underlying bone, and while screws are inserted through the holes into the bone. Tools designed for this task are disclosed as well.

8 Claims, 7 Drawing Sheets

DRILL GUIDE AND PLATE ATTACHMENT MECHANISM FOR ORTHOPEDIC PLATING

BACKGROUND OF THE INVENTION

This invention relates to orthopedic surgery and more particularly to a drill guide and plate attachment mechanism for facilitating orthopedic surgical plating procedures.

Surgical plates in various forms have been used by orthopedic surgeons to fixate bones in a specifically desirable fashion or position such that bone knitting or healing occurs between the juxtaposed bony elements. In this regard, plating is employed across bony fracture sites or across surgical fusion sites to fixate and hold the bone components in a preferred configuration until solid bony union occurs. Because independent movement of the bony elements relative to each other retards or prevents bony union from occurring, bone fixation is frequently required, much like an external cast is used to inhibit motion sufficient to allow healing of a broken arm or leg bone.

The plate allowing fixation of the bony components is generally secured to the bone itself by the use of specifically designed bone screws. Drilling and tapping of bone is frequently required to allow the screws to be appropriately placed. Because surgical plating may be necessary in limited access approaches, drill guides are often used to limit the depth to which the bit itself violates bone, and to prevent injury to deep structures from the rotating drill. After drilling has occurred, the guide is frequently removed so that drilling and tapping of the drill hole can be performed. Once the hole has been drilled and the drill guide has been removed, it is often difficult to find the drill holes site deep within a body cavity. If drilling is done through the plate itself, removal of the guide to allow tapping of the hole and/or screw placement frequently allows sufficient plate movement that the drill hole site is difficult to find. This wastes valuable surgical time and is frustrating for the surgeon or his designate performing this component of the operation.

It would be desirable to have a drill guide which would allow drilling, tapping and screw placement to occur without having to remove, change or reposition the drill guide. It would also be desirable to have a drill guide which would securely hold the plate in position while drilling, tapping and screw placement is occurring.

SUMMARY OF THE INVENTION

An object of the invention is to provide an orthopedic drill guide and attachment mechanism which allows for easier and more accurate screw placement without having to remove or alter the position of the drill guide.

To achieve this end, three specific design alterations are required. The first requirement is that the drill guide attach to the plate external to the screw hole site. This is achieved by arms on the external surface of the tubular component of the guide. These arms are situated 180° from each other and can be approximated either by forcing them together by an external tube slid over the internal tubular component of the drill guide or by a scissor mechanism external to the tubular component of the guide which approximates them.

The second design alteration occurs in the body of the plate itself and specifically at the site of the screw hole. To allow the guide arms to secure the plate, depressions or pits are formed at the sides of the screw hole to allow the external arms to grip and securely hold the drill guide to the plate, or in a double guide barrel design, grip the side of the plate.

By varying the lengths of the arms relative to each other, differing degrees of angulation of drilling and screw placement can occur. The arms can securely hold the plate in the appropriate position and attitude until all components of the fixation procedure have been completed (drilling, tapping, screw placement). Once the screw is secure, the plate is fixed in position and the arms can be disengaged and the drill guide can be removed. For the screw to securely hold the plate to the bone, the screw hole in the plate must be tapered such that a corresponding taper of the head of the screw holds the screw flush with the surface of the plate, or counter sunk to allow easy disengagement of the guide tube.

The third component of the design alteration related to the drills and taps employed with the drill guide. To function appropriately with the guide and plate, the drills and guides must be constructed such that the outer diameter of the shaft of the drill or tap fits snugly within the inner diameter of the drill guide. The actual drill bit or bone tap is of a small diameter which is equal to or less than the diameter of the smallest (deepest) component of the screw hole in the plate. This allows the drill or tap to be held securely while in use in the guide and also prevents drilling or tapping too deeply because the largest diameter of the drill or tap is always greater than the smallest diameter of the tapered screw hole in the plate.

In appropriate sequence, therefore, the plate can be gripped and held by the drill tube guide. Drilling and tapping and screw placement can safely and securely be carried out through the drill guide without need for alteration in position and the guide can be removed once the plate is securely fixed to bone.

BRIEF DESCRIPTION OF THE DRAWINGS

In the accompanying drawings.

DESCRIPTION OF THE PREFERRED EMBODIMENT

A drill guide and plate attachment mechanism embodying the invention includes both a specially designed orthopedic plate 10, shown in FIG. 1, and a drill guide assembly 50, components of which are shown in FIGS. 3–7.

Figure 1A:
FIGS. 1a and 1b are side and plan views, respectively, of a drill guide and plate attachment mechanism embodying the invention.
Figure 1B:
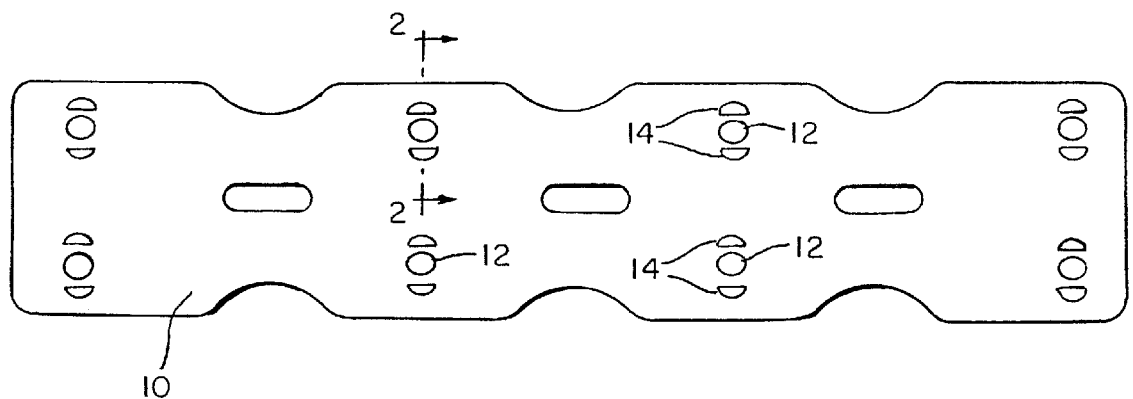

The plate is made of thin metal, such as stainless steel, and may have a slight camber, as shown in FIG. 1a. An array of screw holes 12 are provided, through which screws may be inserted into underlying bone.

Figure 2:
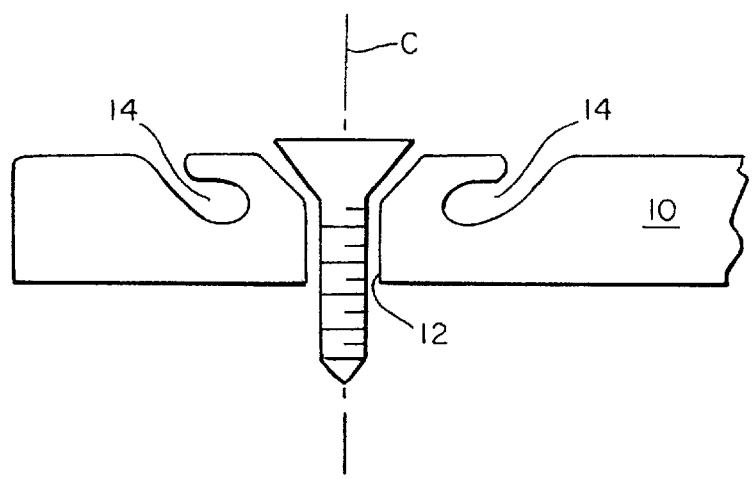
FIG. 2 is a sectional view, taken on plane 2—2 in FIG. 1b, of the plate, with a screw shown in addition.

Before the plate can be attached to the bone, the bone must be drilled at locations corresponding to the positions of the screw holes. To enable the surgeon to hold and position the plate against the bone, and to accurately drill into the bone, the plate has a pair of recesses 14 straddling each hole. These are shown in detail in FIG. 2. Each recess 14 extends at an angle to the centerline "C" of the hole, the opposing recesses being obliquely angled toward one another. The preferred angle is 30° to 60°, most preferably 45°. All edges of the recess are rounded as shown. In the plan view of FIG. 1b, the recesses appear as segments of circles, but that shape could vary, the important thing being that a tool tip can be inserted into the recess.

Figure 3:
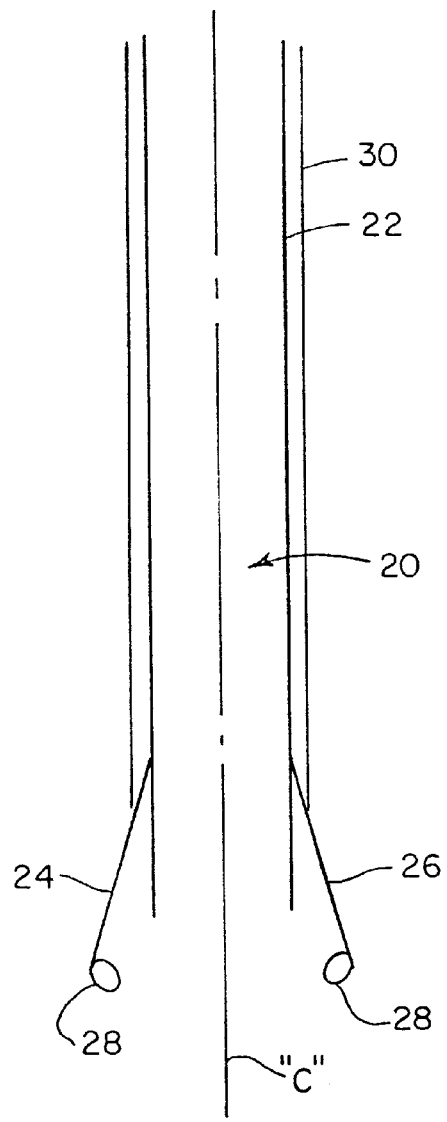
FIG. 3 is a diagrammatic sectional side view of a drill guide assembly adapted to engage the plate.

FIG. 3 shows a tool 20 designed for engaging the recesses 14 in the orthopedic plate. It comprises a guide tube 22 supporting a pair of flexible arms 24, 26 which, when unconstrained, spring outward to the configuration shown in FIG. 3. Each arm has a spherical or rounded tip 28 small enough to enter well into one of the recesses, as illustrated in FIG. 4.

Figure 4:
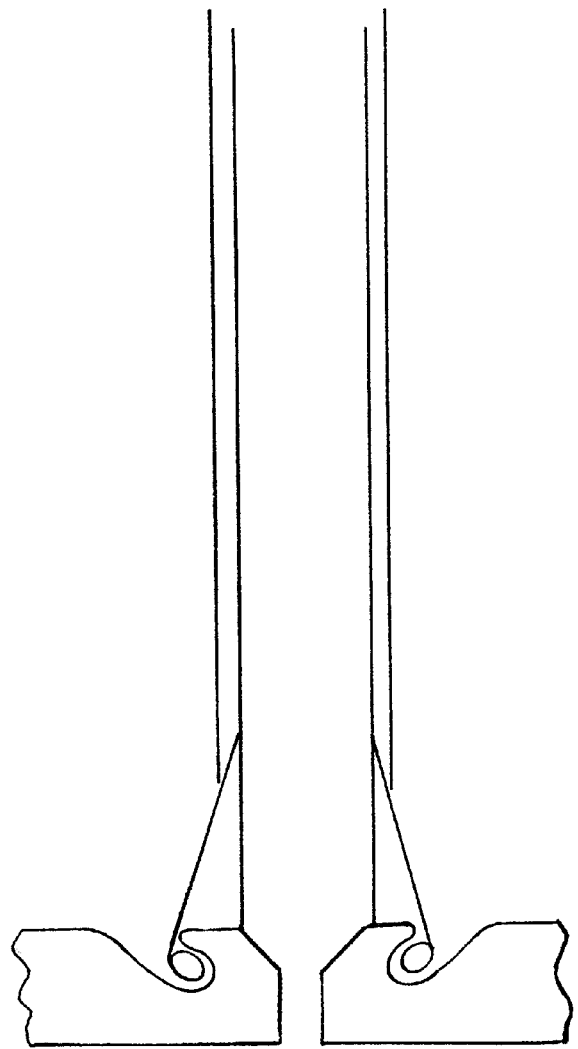
FIG. 4 is a view like FIG. 3, with a guide plate added, showing the arms of the drill guide engaged in depressions straddling the hole.

The external tube 30 which has been slid down over the guide tube in FIG. 4 depresses the arms 24, 26, forcing them toward the centerline, so that they hook into the recesses 14 and grip the plate 10. As long as the external tube is advanced, the plate is held fast, and the surgeon can even use the guide tube assembly as a manipulator for the orthopedic plate as he positions it with respect to the bone.

Figure 5:
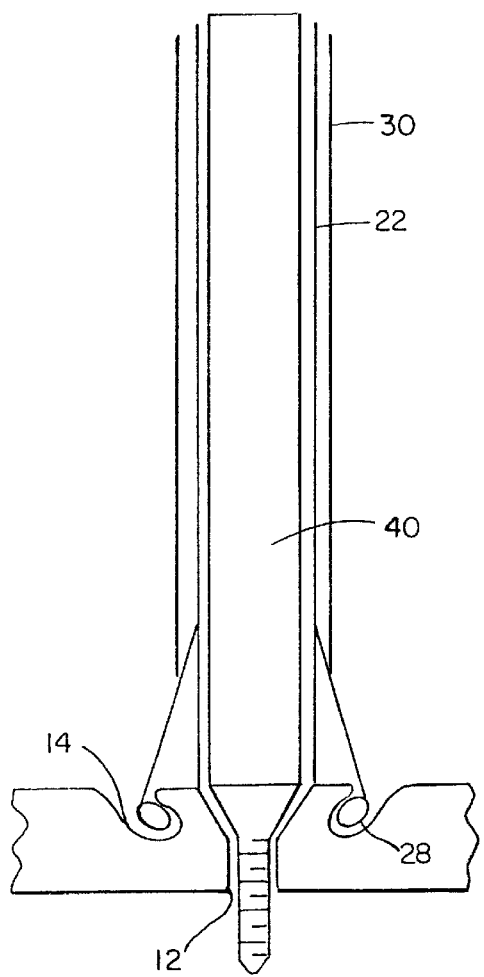
FIG. 5 shows the drill guide with a drill bit in place.
Figure 6:
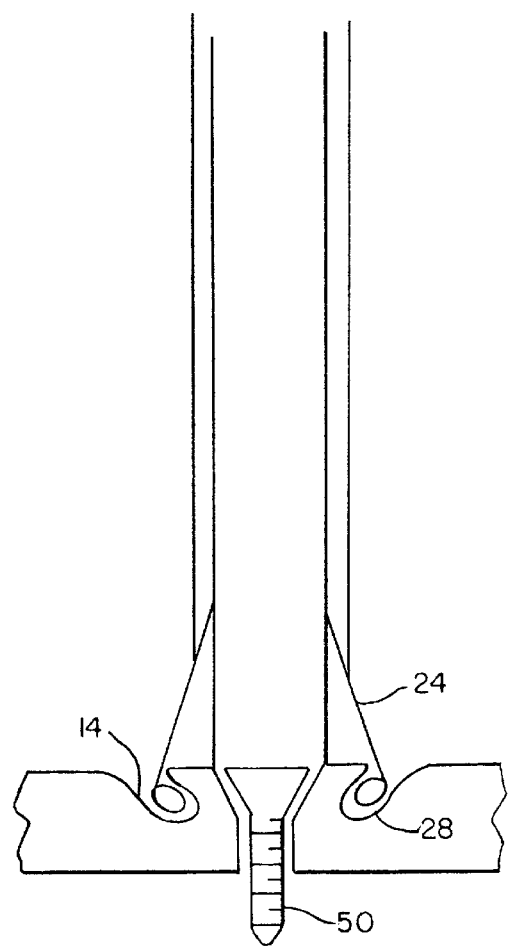
FIG. 6 is a similar view of the drill guide, with the bit removed, and a screw installed in the hole.

When the plate is properly positioned, the surgeon inserts a drill 40 through the guide tube, and drills a hole in the bone, through the screw hole 12 (FIG. 5). Then, after removing the drill, he inserts a screw 50 (FIG. 6) held at the end of a suitable driver, not shown, through the guide tube 22, and screws it into the bone. Now the external tube 70 may be retracted, releasing the arms 24, 26 from the plate.

The above procedure is repeated until the desired number of screws have been placed, leaving the plate firmly secured to the bone.

Figure 7:
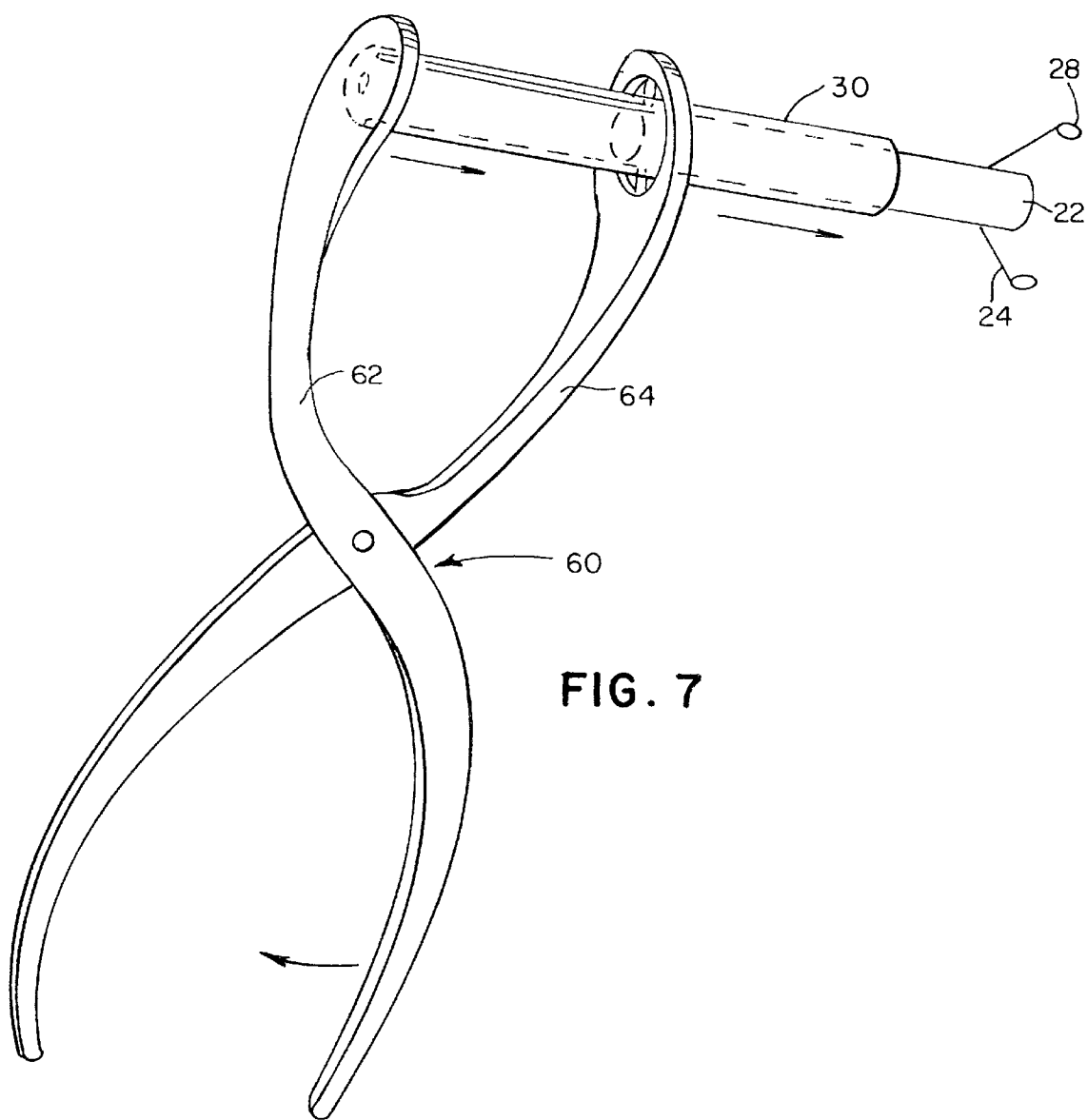
FIG. 7 is a perspective view of a tool for actuating the drill guide.

FIG. 7 shows a preferred tool 60, which has a pair of pivoted levers 62, 64, each lever having a handle end and a working end. The working end of one of the levers has the guide tube 22 affixed to it, and the other end supports the external tube 30. When the handles are squeezed together, the external tube advances over the guide tube, depressing the arms 24, 26 as previously described. A spring (not shown) may be provided to drive the lever to either an open or a closed configuration.

Figure 8:
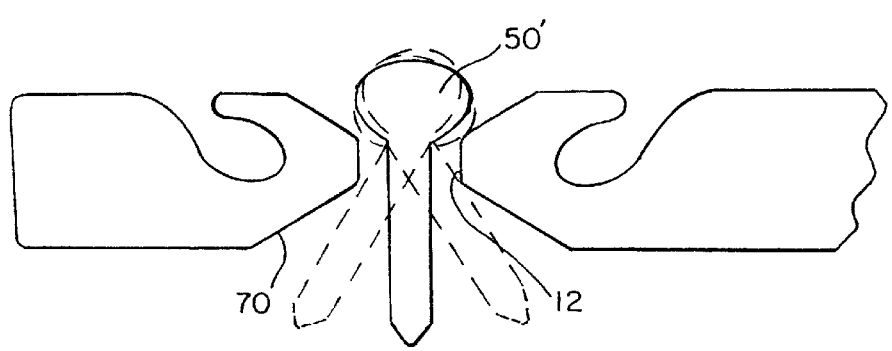
FIG. 8 shows a plate which is countersunk on the bottom to permit the installation of screws are non-perpendicular angles.

In the preceding examples, the hole was shown being drilled perpendicularly with respect to the guide plate. In FIG. 8, however, the bottom 70 of the hole 12 is countersunk, as well as the top, so that round-headed screws 50 can be inserted at various oblique angles, as suggested by the broken lines.

Figure 9:
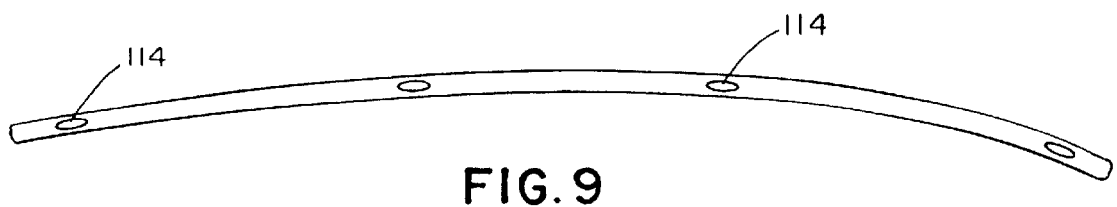
FIG. 9 is a side view of a modified form of the guide plate.
Figure 10:
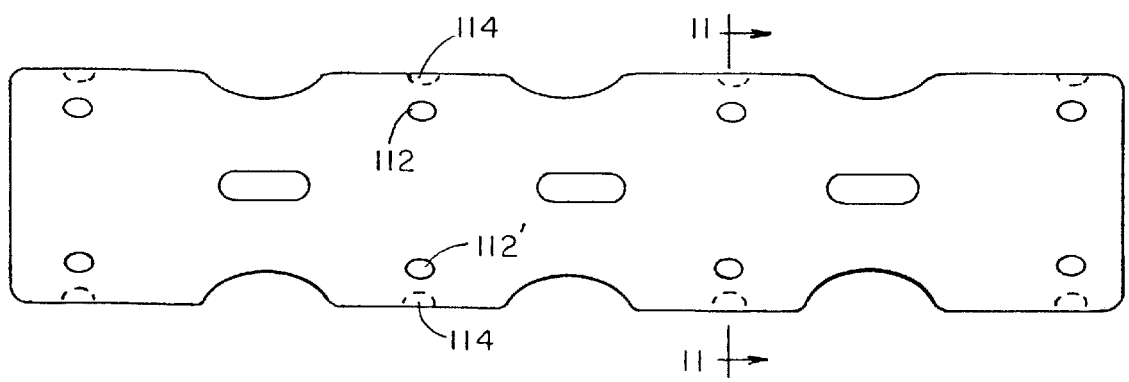
FIG. 10 is a top plan view thereof.
Figure 11:
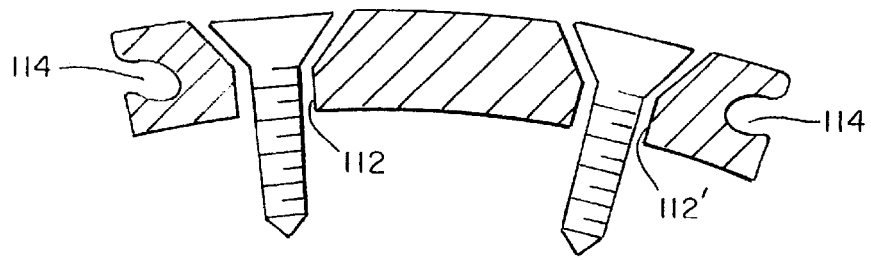
FIG. 11 is a cross-sectional view taken on the line 11—11 in FIG. 10.
Figure 12:
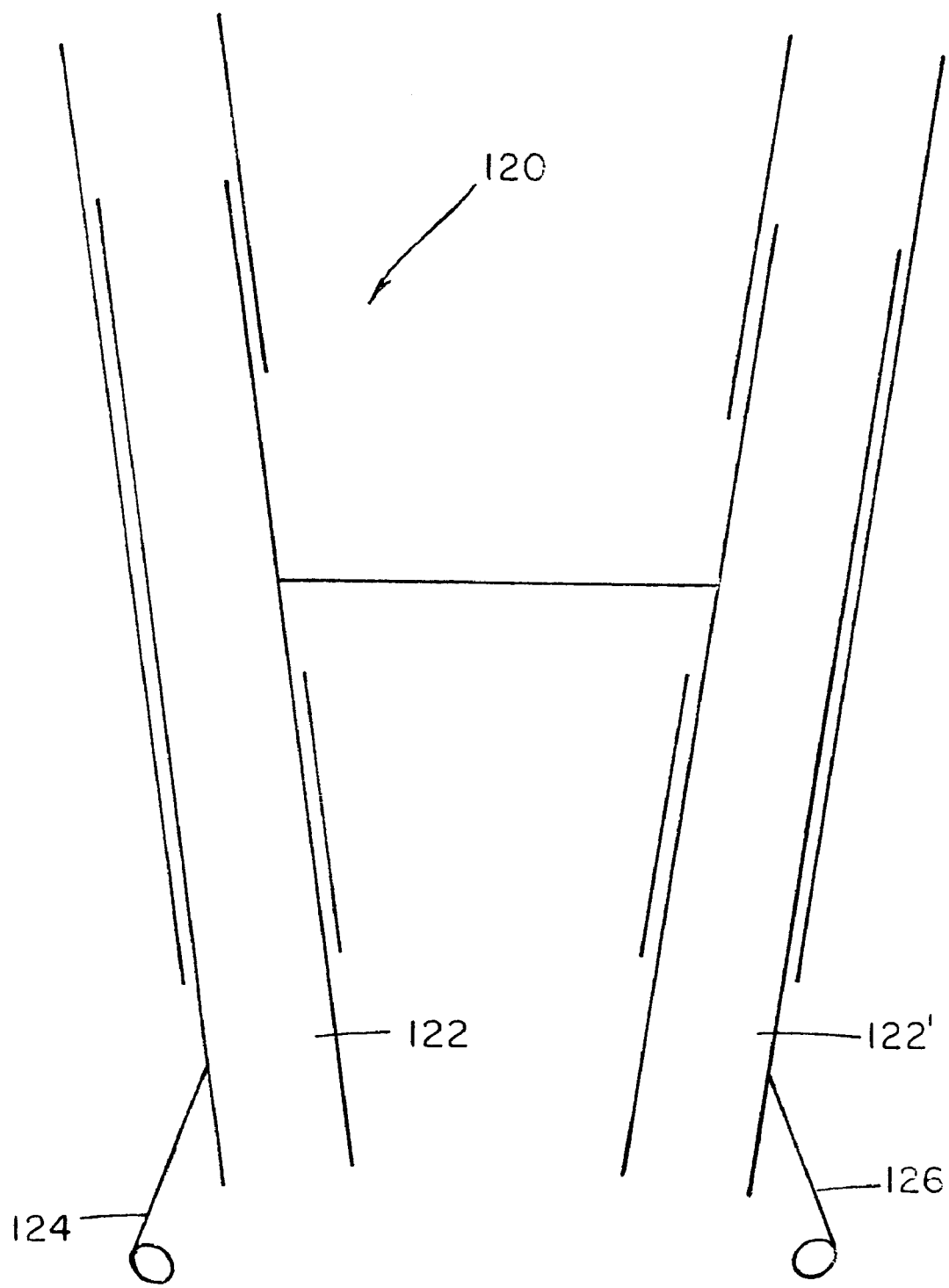
FIG. 12 is a cross-sectional view of a double-barreled drill guide for use with the guide plate shown in FIGS. 9–11.
Figure 13:
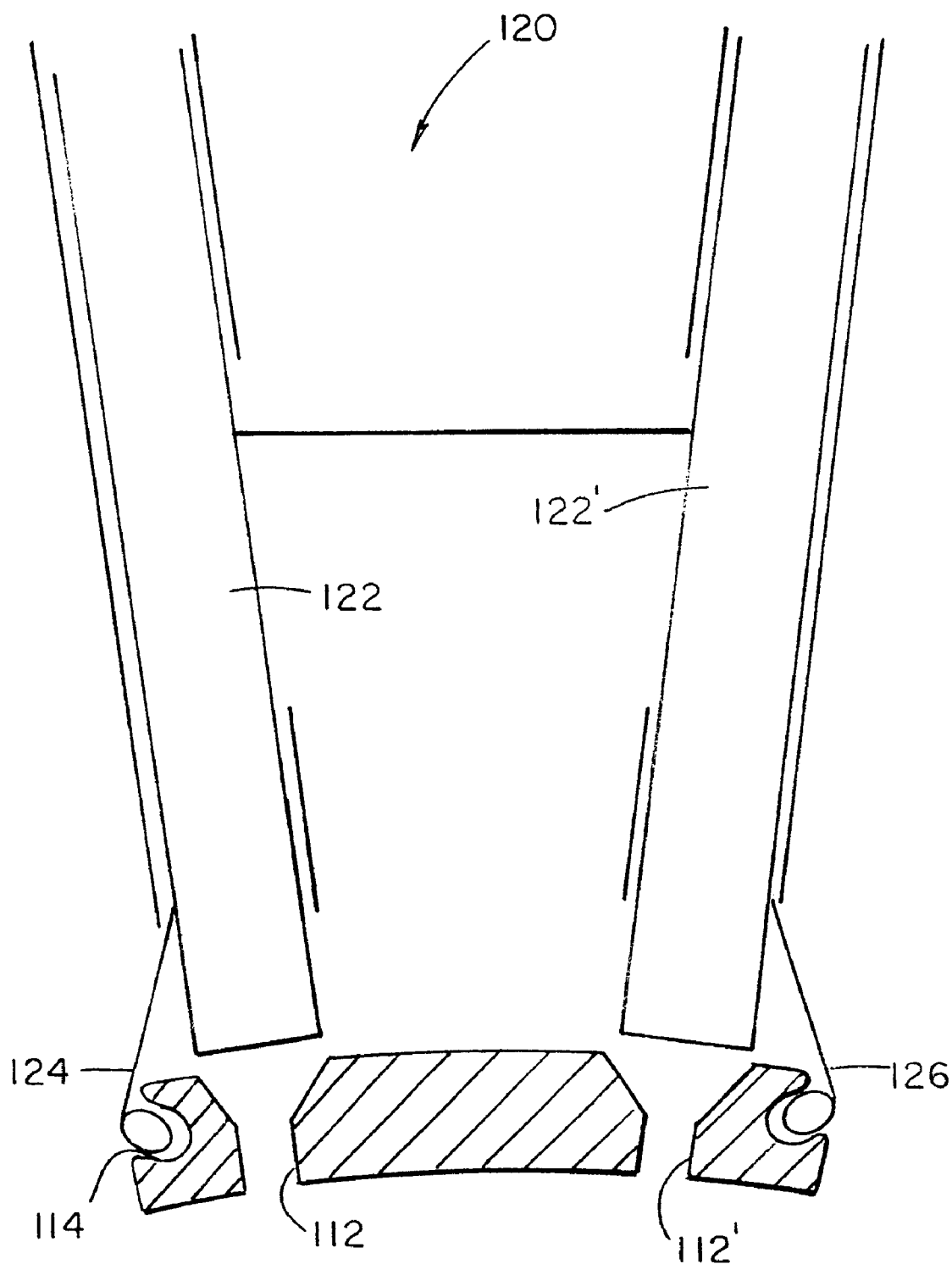
FIG. 13 is a view like FIG. 12, showing the drill guide engaging recesses at the edge of the guide plate.

The guide plate of FIGS. 9–11 is designed for use with a double-barreled drill guide, shown in FIGS. 12–13, which permits the placement of bone screws two at a time. The plate has pairs of recesses 114 formed in its lateral edges, so that each pair straddles a pair of holes 112, 112', rather than one. The recesses and the holes which they are straddle are centered on a common plane, one such plane being the plane 11—11 in FIG. 10. Placement of screws is substantially the same as described for the previous embodiment, except that now two screws are placed at each plane. The placement tool 120, shown in simplified form in FIGS. 12 and 13, includes a pair of guide tubes 122, 122', and a single pair of gripping arms 124, 126 arranged outboard of the guide tubes in a transverse plane (e.g., 11—11) which contains the axes of the guide tubes.

Since the invention is subject to modifications and variations, it is intended that the foregoing description and the accompanying drawings shall be interpreted as only illustrative of the invention defined by the following claims.

I claim:

1. An orthopedic plate having an array of holes therein for receiving screws and for acting as drill guides, the plate being provided with, straddling each of said holes, a pair of recesses adapted to be engaged within by jaws of a gripping tool, the recesses being obliquely angled toward one another, whereby the plate can be grasped with the gripping tool while bone beneath the plate is being drilled and screws are being installed into the holes.

2. The invention of claim 1, wherein each of said recesses has a substantially semicircular shape in plan view.

3. The invention of claim 1, wherein said recesses angle toward one another at an angle of 30° to 60°.

4. The invention of claim 1, wherein said recesses angle toward one another at an angle of about 45°.

5. The invention of claim 1, wherein said recesses have rounded edges.

6. The invention of claim 1, wherein said holes are countersunk on both sides to permit screws to be installed at angles other than perpendicular to the plate.

7. The invention of claim 1, wherein said holes are arranged in pairs, and said recesses are formed in transverse edges of said plates, the holes and the respective recesses being aligned on a common transverse plane.

8. A method of applying an orthopedic plate to a bone, said method comprising steps of providing said plate with holes for receiving screws and opposed recesses straddling said holes into each of which a grasping tool may be inserted, grasping and placing said plate by manipulating said tool, drilling into the bone through said holes while maintaining the grasp on the plate, inserting screws through the holes into the bone while maintaining the grasp on the plate, and then manipulating the tool to release the plate and withdrawing the tool.

* * * * *